United States Patent [19]

Arnold

[11] Patent Number: 5,550,266

[45] Date of Patent: *Aug. 27, 1996

[54] METHOD FOR THE PREPARATION OF PURE CARBOXYETHYL GERMANIUM SESQUIOXIDE

[76] Inventor: Michael J. Arnold, 4521 Campus Dr., Suite 225, Irvine, Calif. 92715

[*] Notice: The term of this patent shall not extend beyond the expiration date of Pat. No. 5,386,046.

[21] Appl. No.: 381,343

[22] Filed: Jan. 31, 1995

Related U.S. Application Data

[63] Continuation-in-part of Ser. No. 204,548, Mar. 2, 1994, Pat. No. 5,386,046.

[51] Int. Cl.$^6$ ............................................. C07F 7/30
[52] U.S. Cl. ........................... 556/89; 556/87; 556/105
[58] Field of Search .............................. 556/87, 89, 105

[56] References Cited

U.S. PATENT DOCUMENTS

| | | | |
|---|---|---|---|
| 3,793,455 | 2/1974 | Asai et al. | 424/287 |
| 4,066,678 | 1/1978 | Sato et al. | 260/429 R |
| 4,473,581 | 9/1984 | Ishida et al. | 424/287 |
| 4,898,882 | 2/1990 | Nagahama et al. | 514/492 |
| 4,956,272 | 9/1990 | Kakimoto et al. | 435/1 |
| 4,973,553 | 10/1990 | Miyao et al. | 435/206 |

FOREIGN PATENT DOCUMENTS

| | | |
|---|---|---|
| 0160319 | 12/1979 | Japan . |
| 0128789 | 10/1981 | Japan . |
| 0067588 | 4/1982 | Japan . |
| 1148186 | 7/1986 | Japan . |
| 2190835 | 12/1987 | United Kingdom . |
| 2222404 | 3/1990 | United Kingdom . |

*Primary Examiner*—Porfirio Nazario-Gonzales
*Attorney, Agent, or Firm*—Lawrence S. Cohen; Freilich, Hornbaker & Rosen

[57] ABSTRACT

A synthetic method for generating pure carboxyethyl germanium sesquioxide in the absence of toxic impurities. In the method germanium dioxide and metallic germanium are not used as starting materials. The method involves steps which ensure (a) full reaction of germanium tetrachloride to ensure none is available to form germanium dioxide, (b) removal of any germanium dioxide, (c) removal of any germanium tetrachloride later produced from any germanium dioxide and (d) final removal of any germanium dioxide.

14 Claims, No Drawings

METHOD FOR THE PREPARATION OF PURE CARBOXYETHYL GERMANIUM SESQUIOXIDE

This application is a continuation-in-part of application Ser. No. 204,548, filed Mar. 2, 1994, now U.S. Pat. No. 5,386,046 issued Jan. 31, 1995 the content of which is incorporated herein by this reference.

BACKGROUND

1. Field of the Invention

The present invention relates to a synthetic method for generating pure carboxyethyl germanium sesquioxide, and in particular to a chemical method for synthesizing carboxyethyl germanium sesquioxide that yields the carboxyethyl germanium sesquioxide without trace amounts of germanium dioxide or metallic germanium.

2. Background of the Invention

Carboxyethyl germanium sesquioxide (organic germanium) has been shown to have chemotherapeutic value. Nakao Ishida, et. al., U.S. Pat. No. 4,473,581 teach that carboxyethyl germanium sesquioxide can induce interferon production in humans. Nagahama teaches in U.S. Pat. No. 4,898,882 that carboxyethyl germanium sesquioxide can provide the human body resistance against the common cold. Asai in U.S. Pat. No. 3,793,455 describes the use of carboxyethyl germanium sesquioxide as an agent for treatment of hypertension. Although carboxyethyl germanium sesquioxide is a well known compound, its molecular structure has been shown to be dependent on the synthetic method employed.

For use as a chemotherapeutic agent, or as a food supplement, it is required that carboxyethyl germanium sesquioxide be pure, free of unwanted and potentially lethal contaminants germanium dioxide and metallic germanium. Many known methods for synthesizing carboxyethyl germanium sesquioxide provide for the production of germanium sesquioxide contaminated with trace amounts of metallic germanium, or germanium dioxide, since these are used as the starting materials. Trichlorogermanium acrylate moieties (trichlorogermanium acroyl chlorides, trichlorogermanium acrylic acids, trichlorogermanium acroleins and trichlorogermanium alkyl acrylates) are the key intermediates common to such known synthetic routes. Entries described by the prior art to the trichlorogermanium acrylate intermediates, utilize methods that require either oxidation of metallic germanium with hydrochloric acid, or reduction of germanium dioxide and, hence, the probability of the presence of trace amounts of unreacted starting material (metallic germanium or germanium dioxide) in the product is significant.

The present invention does not start with either metallic germanium or germanium dioxide, but rather starts with germanium tetrachloride.

SUMMARY OF THE INVENTION

Accordingly, a major object of the present invention is the provision of a synthetic method that is devoid of the aforementioned drawbacks which to date have characterized this art.

It is the primary object of the present invention to provide a method whereby carboxyethyl germanium sesquioxide can be prepared without contamination from metallic germanium or germanium dioxide.

It is another object of the present invention to provide a method for the production of a carboxyethyl germanium sesquioxide molecular species that is completely non toxic to the human body.

It is another object of the present to provide a method for the production of a carboxyethyl germanium sesquioxide molecular species that has an $LD_{50}$ value of at least 5g/Kg.

The present method involves the isolation and purification of the intermediate trichlorogermane propionic acid (hereafter referred to as TPA). In this method reaction of germanium tetrachloride in the presence of acrylic acid takes place under ambient conditions to form a mixture of polymeric material and TPA. This mixture is then depolymerized with concentrated hydrochloric acid to form a crude TPA reaction product, which is then recrystallized to a pure TPA form. The pure TPA is then hydrolyzed to form carboxyethyl germanium sesquioxide.

In an alternative method the recrystallization step is omitted. Instead, after the mixture is depolymerized with concentrated hydrochloric acid to form a crude TPA reaction product as a white amorphous solid, it is directly hydrolyzed to form carboxyethyl germanium sesquioxide.

DETAILED DESCRIPTION OF THE INVENTION

The method of the invention involves the steps of forming from the starting material of germanium tetrachloride, an intermediate material, trichlorogermane propionic acid, isolating and purifying the trichlorogermane propionic acid and converting the TPA by hydrolysis to carboxyethyl germanium sesquioxide.

The specific steps of the process are described as follows:

a first mixture is obtained by reacting germanium tetrachloride with tetramethyl disiloxane and acrylic acid. This first mixture consists essentially of trichlorogermane propionic acid (TPA), a polymer and volatile by-products. The reaction profile is:

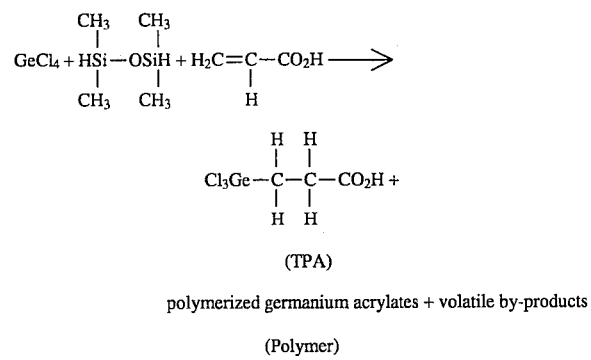

The first mixture is subjected to vacuum distillation to remove the volatiles. This results in a second mixture which consists essentially of TPA plus the polymerized germanium acrylates (hereafter referred to as "polymer"). The chemical profile of this steps is:

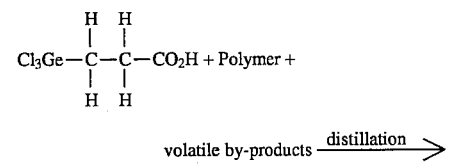

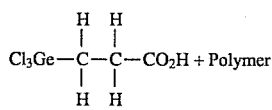

The second mixture is reacted with hydrochloric acid in sufficient amount, preferably in excess, to completely react with the polymer for depolymerization, that is to convert the polymer to TPA providing a third mixture consisting essentially of TPA and hydrochloric acid. That is, it is a heterogeneous mixture of white solid TPA and aqueous HCL (conc). The reaction profile is:

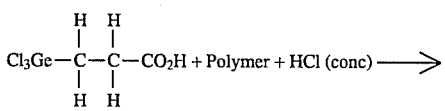

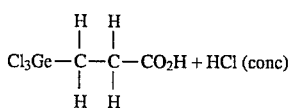

The third mixture is subjected to solvent extraction to separate the hydrochloric acid from the TPA and provide a fourth mixture consisting essentially of TPA and extraction solvent. The preferred solvent is a sufficient amount, preferably in excess, of a halogenated solvent, specifically dichloromethane being most preferred. Chloroform and carbotetrachloride might also work. The reaction profile is:

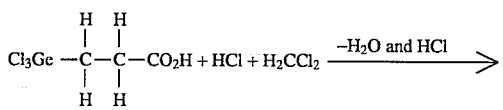

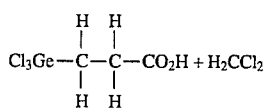

The fourth mixture is subjected to vacuum distillation to remove the solvent ($H_2CCl_2$) resulting in a crude reaction product, consisting essentially of TPA. That is, the TPA is in a form or mixture presumed to be insufficiently pure. The reaction profile is:

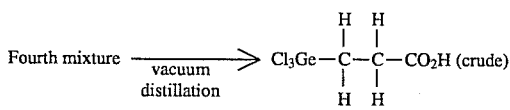

Next the crude TPA reaction product is purified and converted to carboxyethyl germanium sesquioxide by the following steps:

The crude TPA reaction product is dissolved in a minimal amount of boiling non-polar alkyl solvent, preferably hexane, to form upon cooling, high purity crystals of TPA. The hexane is removed and the resulting crystals are washed successively with hexane in order to yield fine pure crystals of TPA. The reaction profile is:

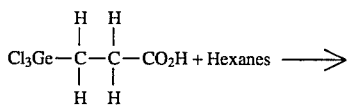

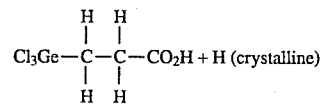

This results in pure crystals of TPA

Next the pure TPA crystals are reacted in a sufficient amount, preferably in excess, of ammonium hydroxide, to form a fifth mixture consisting of hydrolyzed TPA. Slow addition of concentrated sulfuric acid yields carboxyethyl germanium sesquioxide. The chemical profile is:

Fifth mixture+$H_2 SO_4$ (conc)→$Ge_2 C_O H_{10} O_7$

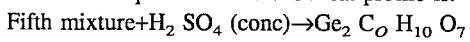

A one-pot synthesis of analytically pure organic germanium is described below.

To a 2 L round bottom flask purged with argon was added successively: germanium tetrachloride (200 g [0.9346 mol]), tetramethyl disiloxane (125 g[0.93 mol]), and acrylic acid (70.0 g[0.97 mol]). The reaction flask was purged with argon then sealed by placement of a ground glass stopper with a teflon sleeve and secured via teflon tape. The slightly cloudy mixture changed to a clear, colorless homogeneous solution within about 2 hours, and this was stirred for seven days at ambient temperature. The volatile components were removed via vacuum (0.5 to 5 mmHg) while the product mixture was heated to an internal temperature of 70° C.–80° C., where it was a homogeneous, clear and colorless viscous solution (melt). Evacuation was continued until no more distillate was observed (ca. 2 hours). This was cooled to an ambient temperature to yield a white amorphous solid. To this was added 950 mL of concentrated HCl. The resulting heterogeneous mixture was warmed to an internal temperature of 60° C.–70° C., and stirred for four hours. The cooled mixture was extracted 3 times with 500 mL of dichloromethane. The combined extracts were evaporated under reduced pressure via rotary evaporator to give a while amorphous solid. This was dissolved in ca. 1 L boiling hexane (until a clear colorless homogeneous hot solution was obtained), and let cool gently to ambient temperature. The product, trichlorogermane propionic acid, was isolated via suction filtration, washed once with hexane to give fine prisms, mp 75° C.–79° C. This was immediately taken up (vigorous reaction), with careful addition of 850 mL of ammonium hydroxide (29% ammonia). The resulting turbid mixture was stirred for 4 days at ambient temperature (the mixture changes to a clear, colorless homogeneous solution within 3 hours). To this homogeneous solution was added dropwise over two hours through a reflux condenser 400 mL of concentrated sulfuric acid. NOTE: This is a very vigorous reaction and should be handled with extreme care. A white precipitate formed after addition of ca. 375 mL of acid. The pot was stirred for 48 hours, and then the white solid was isolated via suction filtration, washed successively with 2×150 mL water, 1×150 mL acetone, and 1×200 mL of diethyl ether, then this brilliant white solid was air dried overnight, and then taken up with 150 mL hot water, then cooled and filtered to yield 78.84 g (50%) of analytically pure carboxyethyl germanium sesquioxide.

In an alternative method, the same steps as described above are taken, except that the recrystallization step is omitted. In this alternative method, after the mixture is depolymerized with concentrated hydrochloric acid to form TPA and the hydrochloric acid removed, and the resulting mixture, which is referred to above as the fourth mixture is cleansed of solvent it is then directly hydrolyzed and acidified to form carboxyethyl germanium sesquioxide.

An example of this alternative process follows. To a 50 L glass reactor was added successively: 7.2 Kg germanium tetrachloride, 5.3 Kg tetramethyl disiloxane, and 2.32 Kg of acrylic acid. The resulting mixture was stirred for 5 days forming TPA (trichlorogermane propionic acid) as a product. Volatile components were removed via vacuum distillation while the TPA product was heated to an internal temperature of 75° C.–80° C., where it was a homogeneous, clear and colorless viscous melt. Distillation is continued until no more distillate appears. The product was then cooled to ambient temperature yielding a white amorphous solid of TPA. To this was added 35 L of concentrated HCl. The resulting heterogeneous mixture was warmed to an internal temperature of 60° C.–70° C., and stirred for four hours and allowed to cool. The cooled mixture was extracted 3 times with 25 L of dichloromethane. The dichloromethane was removed with vacuum distillation at 40° C. to give a white amorphous solid. The white amorphous solid, crude TPA, was then hydrolyzed to carboxyethyl germanium sesquioxide. To this end the crude TPA was immediately taken up (vigorous reaction), with careful addition of 30 L of ammonium hydroxide (29% ammonia). The resulting mixture was stirred for 4 days at ambient temperature. To this, 14.4 L of concentrated sulfuric acid was added dropwise over two hours through a reflux condenser producing a white solid of carboxyethyl germanium sesquioxide. The white solid was isolated via suction filtration, washed successively with 2×5.4 L acetone, and 2×5.4 L of diethyl ether, then the resulting brilliant white solid was air dried overnight, and then taken up with 9 L of hot water, then cooled and filtered to yield carboxyethyl germanium sesquioxide.

In the production of organic germanium for human consumption such as a food supplement there is concern about the possible presence of metallic germanium and germanium dioxide. In the present invention, including either of the methods described above, there can be no metallic germanium because the starting materials and methods do not have the potential for producing any metallic germanium. In respect of germanium dioxide, the first procedure, in particular the recrystallization step will eliminate any potential for the presence of germanium dioxide. In respect of the second method, the procedures effectively eliminate any reasonable possibility of the presence of germanium dioxide. The basis for this conclusion is now explained. Any germanium dioxide found in the product as synthesized in this method would have as its precursor the germanium tetrachloride. In the initial reaction of germanium tetrachloride with tetramethyl disiloxane and acrylic acid it is theoretically possible that there remains unreacted germanium tetrachloride (considered to be part of the volatile byproducts) which would have the theoretical potential to hydrolyze to form germanium dioxide. Thus there is a theoretical possibility of the presence of germanium dioxide, which is a solid.

The next step of vacuum distillation would remove any remaining unreacted germanium tetrachloride. Also, any germanium dioxide in the aqueous phase is removed and discarded as noted this is done three times for thoroughness.

The next reaction, with hydrochloric acid would convert any then present germanium dioxide to germanium tetrachloride.

The next step of solvent extraction with dichloromethane will allow any germanium dioxide in the organic to be observed (as a solid) and in the laboratory testing, none has been observed (germanium dioxide is insoluble in dichloromethane). Therefore it is concluded that no germanium dioxide is present in the organic phase.

The next step of vacuum distillation would remove any remaining germanium tetrachloride that had been formed, thus precluding any subsequent formation of germanium dioxide.

It can be appreciated that in general there is only the barest theoretical possibility of the formation of germanium dioxide or its presence in the end product. With the steps employed even this possibility is obviated. Therefore this method is seen as providing a resulting product of sufficient purity for human consumption.

As compared to the first procedure, the second procedure has at least two important advantages. The first advantage refers to avoiding the use of hexane. Hexane is a volatile organic contaminant (VOC); an atmospheric contaminant. It is also dangerously explosive. Therefore its elimination is salutary.

Secondly, the recrystallization step adds a substantial amount of time and labor to the manufacturing process; its elimination providing the concomitant benefits.

In use carboxyethyl germanium sesquioxide is believed to have beneficial effects for humans. For example it is believed to stimulate the production of interferon. With regular use a 100 mg/day dosage is appropriate. With flu symptoms 1,000 mg/day has been recommended. It is a stable compound and may be combined with other energy source type supplements. It is compatible with commonly used excipients such as maltodextrin and microcrystalline cellulose.

An exemplary mixture of a food supplement using organic germanium is:

| | |
|---|---|
| Pangamic acid | 50 mg. |
| Organic germanium | 25 mg. |
| Co Enzyme Q10 | 25 mg. |
| Vitamin A | 1,250 I.U. |
| Vitamin E | 100 I.U. |
| Vitamin D | 7.5 I.U. |
| Vitamin K | 125 mg. |

Although particular embodiments of the invention have been described and illustrated herein, it is recognized that modifications and variations may readily occur to those skilled in the art, and consequently it is intended that the claims be interpreted to cover such modifications and equivalents.

What is claimed is:

1. A method of preparing organic germanium in the absence of any toxic level of germanium dioxide or metallic germanium comprising;

preparing trichlorogermane propionic acid as a crude reaction product from germanium tetrachloride;

forming a germanium acrylate moiety as a reaction product from hydrolysis of the reaction product;

forming carboxyethyl germanium sesquioxide as a reaction product from acidification of the germanium acrylate moiety.

2. The method of claim 1 wherein the trichlorogermanium propionic acid is subject to vacuum distillation.

3. The method of claim 1 wherein the acidifying step is slow addition of concentrated sulfuric acid.

4. A method of preparing organic germanium in the absence of any toxic level of germanium dioxide or metallic germanium comprising;

reacting germanium tetrachloride, acrylic acid and tetramethyl disiloxane to obtain first reaction products in a first mixture;

removing volatiles from the first mixture to obtain a second mixture;

reacting the second mixture with at least an effective amount of hydrochloric acid to obtain a third mixture consisting essentially of trichlorogermane propionic acid and hydrochloric acid;

separating by extraction with an organic solvent the trichlorogermane propionic acid from the hydrochloric acid in the third mixture to form a fourth mixture;

removing the extraction solvent from the fourth mixture to form a reaction product of trichlorogermane propionic acid;

hydrolyzing the reaction product of trichlorogermane propionic acid in ammonium hydroxide to form a fifth mixture;

reacting the fifth mixture with slow addition of concentrated sulfuric acid to form carboxyethyl germanium sesquioxide.

5. A method of preparing pure organic germanium in the absence of germanium dioxide or metallic germanium comprising;

preparing trichlorogermane propionic acid as a crude reaction product from materials not including either germanium dioxide or metallic germanium;

forming carboxyethyl germanium sesquioxide as a reaction product from hydrolysis of the trichlorogermane propionic acid.

6. The method of claim 5 wherein said materials comprise germanium tetrachloride, acrylic acid and tetramethyl disiloxane.

7. The method of claim 4 wherein an excess of reactant with the germanium tetrachloride is used to ensure full reaction of the germanium tetrachloride.

8. The method of claim 4 wherein the volatiles include any unreacted germanium tetrachloride and the volatiles are removed by vacuum distillation to ensure removal of any unreacted germanium tetrachloride.

9. The method of claim 4 wherein any germanium dioxide in the first mixture is converted to germanium tetrachloride in the reaction with hydrochloric acid.

10. The method of claim 9 in which an excess amount of hydrochloric acid is used to ensure reaction of any germanium dioxide to germanium tetrachloride.

11. The method of claim 4 wherein the organic solvent is dichloromethane.

12. The method of claim 11 wherein the extraction solvent is removed by vacuum distillation.

13. The method of claim 11 wherein the fourth mixture is observed for any solid germanium dioxide.

14. The method of claim 4 wherein the extraction solvent in the fourth mixture is considered to include any germanium tetrachloride and the extraction solvent is removed by vacuum distillation to ensure removal of any germanium tetrachloride.

* * * * *